United States Patent [19]

Cragoe, Jr. et al.

[11] 4,091,107

[45] May 23, 1978

[54] 8-AZA-9-OXO(AND DIOXO)-THIA-11,12-SECOPROSTAGLAN-DINS

[75] Inventors: Edward J. Cragoe, Jr., Lansdale; James H. Jones, Blue Bell, both of Pa.

[73] Assignee: Merck & Co., Inc., Rahway, N.J.

[21] Appl. No.: 741,074

[22] Filed: Nov. 11, 1976

Related U.S. Application Data

[60] Division of Ser. No. 669,123, Mar. 22, 1976, Pat. No. 4,033,996, which is a continuation-in-part of Ser. No. 580,497, May 23, 1975, abandoned, which is a continuation-in-part of Ser. No. 418,341, Nov. 23, 1973, abandoned, which is a continuation-in-part of Ser. No. 354,273, Apr. 25, 1973, abandoned.

[51] Int. Cl.$^2$ .................. C07C 143/74; C07C 143/75; C07C 145/02; A61K 31/195

[52] U.S. Cl. .................. 424/274; 260/326.5 FM; 260/401; 260/514 J; 424/311; 424/319; 542/416; 550/121; 550/125

[58] Field of Search .......... 260/468 D, 468 J, 514 D, 260/514 J, 326.5 FM, 401, 240; 424/311, 319, 274

[56] References Cited

U.S. PATENT DOCUMENTS 3,991,106 11/1976 Cragoe et al. ................ 260/514

*Primary Examiner*—Robert Gerstl
*Attorney, Agent, or Firm*—Thomas E. Arther; Harry E. Westlake, Jr.; Rudolph J. Anderson, Jr.

[57] ABSTRACT

This invention relates to 8-aza-9-ozo(and dioxo)-thia-11,12-secoprostaglandins and processes for their manufacture. These compounds have prostaglandin-like biological activity and are particularly useful as renal vasodilators, for the prevention of thrombus formation, to induce growth hormone release, and as regulators of the immune response.

11 Claims, No Drawings

8-AZA-9-OXO(AND DIOXO)-THIA-11,12-SECOPROSTAGLANDINS

RELATIONSHIP TO OTHER APPLICATIONS

This is a division of application Ser. No. 669,123 filed Mar. 22, 1976; now U.S. Pat. No. 4,033,996 which in turn is a continuation-in-part of Ser. No. 580,497 filed May 23, 1975, now abandoned; which in turn is a continuation-in-part of Ser. No. 418,341 filed Nov. 23, 1973, now abandoned and which in turn is a continuation-in-part of Ser. No. 354,273 filed Apr. 25, 1973, now abandoned.

SUMMARY OF THE INVENTION

This invention relates to novel 8-aza-9-oxo(and dioxo)thia-11,12-secoprostaglandins of the formula

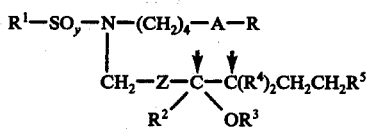  I wherein R is selected from the group consisting of carboxy and a carboxy salt which incorporates a pharmaceutically acceptable cation, such as metal cations derived from alkali metals, alkaline earth metals, and amines such as ammonia, primary and secondary amines and quarternary ammonium hydroxides. Especially preferred metal cations are those derived from alkali metals, e.g. sodium, potassium, lithium, and the like, and alkaline earth metals, e.g., calcium, magnesium, and the like and other metals, i.e., aluminum, iron and zinc.

Pharmaceutically acceptable cations derived from primary, secondary, or tertiary amines, or quaternary ammonium hydroxides are methylamine, dimethylamine, trimethylamine, ethylamine, N-methylhexylamine, benzylamine, α-phenethylamine, ethylenediamine, piperidine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, tetramethylammonium hydroxide, tetraethylammonium hydroxide, benzyltrimethylammonium and the like.

R is also selected from alkoxycarbonyl (—COOY) wherein Y is alkyl having 1–10 carbon atoms, 1-succinimidoethyl, 1-pivaloyloxyethyl, 2-acetamidoethyl or diloweralkyl-aminoloweralkyl; carbamoyl (—CONH$_2$); substituted carbamoyl (—CONR$^6$R$^7$) wherein R$^6$ and R$^7$ are selected from the group consisting of hydrogen, lower alkyl having 1–4 carbon atoms and diloweralkylaminoalkyl having 4–7 carbon atoms; and carbazoyl (—CONH NH$_2$).

A is selected from the group consisting of ethylene (—CH$_2$CH$_2$—), trimethylene (—CH$_2$CH$_2$CH$_2$—), α-methylethylene (—CH$_2$—CH(CH$_3$) —), β-methylethylene (—CH(CH$_3$)CH$_2$—), α,α-dimethylethylene (—CH$_2$—C(CH$_3$)$_2$—), β,β-dimethylethylene (—C(CH$_3$)$_2$CH$_2$—) and oxymethylene (—O—CH$_2$—). (Note that when A consists of a two carbon bridge, the term "α" refers to the carbon adjacent to R, while "β" refers to the other carbon atom.)

R$^1$ is selected from the group consisting of methyl, ethyl, propyl and isopropyl.

Z is selected from the group consisting of ethylene (—CH$_2$—CH$_2$—), vinylene (—CH=CH—), and ethynylene (—C{C—).

R$^2$ is independently selected from the group consisting of hydrogen, methyl, ethyl, or propyl.

R$^3$ is selected from the group consisting of hydrogen and lower alkanoyl of 1–5 carbon atoms, e.g., formyl, acetyl, propionyl, butyryl, isobutyryl, valeryl, pivaloyl, and the like.

R$^4$ is selected from the group consisting of hydrogen and methyl.

R$^5$ is selected from the group consisting of hydrogen; lower alkyl of 1–4 carbon atoms either straight or branched chain (e.g., methyl, ethyl, propyl, isopropyl, butyl, tert-butyl); vinyl; and 2,2,2-trifluoroethyl.

In addition, when R$^5$ is lower alkyl and R$^2$ is methyl, they can be joined together (with abstraction of hydrogen) to form a carbocyclic ring with from 6 to 9 members.

Also, when R$^5$ is lower alkyl and R$^2$ is hydrogen, R$^5$ can be joined to the carbon atom bearing R$^2$ and OR$^3$ to form a carbocyclic ring with from 5 to 8 members.

y is 1 or 2.

It is to be noted that the carbon bearing R$^2$ and OR$^3$ is asymmetric. This invention includes stereoisomers in which this asymmetric center is exclusively is either one or the other of the two possible configurations, R and S.

It is to be recognized that, in some instances, the carbon atoms marked by a dagger ( ) are chiral. In addition, certain carbon atoms included in R$^5$ are also chiral. The compounds of this invention are understood to include the individual stereoisomers and mixtures of stereoisomers, the biological activity of which will vary but which may readily be determined in the in vitro and in vivo assays described hereinbelow.

A preferred embodiment of this invention relates to the 8-aza-9-oxo(and dioxo)thia-11,12-secoprostaglandins having the following general formula:

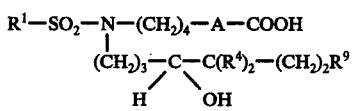  II wherein R$^1$, A, and R$^4$ are as defined in formula I and R$^9$ is lower alkyl of 1–4 carbon atoms. An even more preferred embodiment encompasses compounds of formula II, wherein R$^1$ is methyl or ethyl; A is ethylene or oxymethylene; and R$^9$ is ethyl, isopropyl, or butyl. In addition, another preferred embodiment includes compounds of formula II, wherein R$^9$ is joined to the carbon bearing H, OH to form a carbocyclic ring with from 6 to 9 members.

BACKGROUND OF THE INVENTION

The compounds of formula I are described as 8-aza-9-oxo(and dioxo)thia-11,12-secoprostaglandins because of their structural relationship to the naturally-occurring prostaglandins.

The prostaglandins constitute a biologically prominent class of naturally-occurring, highly-functionalized C$_{20}$ fatty acids which are anabolized readily in a diverse array of mammalian tissues from three essential fatty acids; namely, 8,11,14-eicosatrienoic acid; 5,8,11,14-eicosatetraenoic acid; and 5,8,11,14,17-eicosapentaenoic acid. Each known prostaglandin is a formal derivative of the parent compound, termed "prostanoic acid"; the latter is a $C_{20}$ fatty acid covalently bridged between carbons 8 and 12 such as to form a trans, vicinally-substituted cyclopentane in which the carboxy-bearing side chain is "alpha" or below the plane of the ring and the other side chain is "beta" or above the plane of the ring as depicted in formula III:

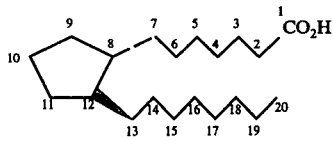

Prostaglandins have been shown to occur extensively in low concentrations in a myriad of mammalian tissues where they are both rapidly anabolized and catabolized and to exhibit a vast spectrum of pharmacological activities including prominent roles in (a) functional hyperemia, (b) the inflammatory response, (c) the central nervous system, (d) transport of water and electrolytes, and (e) regulation of cyclic AMP. Further details concerning the prostaglandins can be found in recent reviews of their chemistry [J. E. Pike, Fortschr. Chem. Org. Naturst., 28, (1970) and G. F. Bundy, A. Rep. in Med. Chem., 7, 157 (1972)], biochemistry [J. W. Hinman, A. Rev. Biochem., 41, 161 (1972)], physiological significance [E. W. Horton, Physiol. Rev., 49, 122 (1969)] and general clinical application [J. W. Hinman, Postgrad. Med. J., 46, 562 (1970)].

The potential application of natural prostaglandins as medicinally useful therapeutic agents in various mammalian disease states is obvious but suffers from three formidable major disadvantages; namely, (a) prostaglandins are known to be rapidly metabolized in vivo in various mammalian tissues to a variety of metabolites which are devoid of the desired original biological activitives, (b) the natural prostaglandins are inherently devoid of biological specificity which is requisite for a successful drug, and (c) although limited quantities of prostaglandins are presently produced by both chemical and biochemical processes, their production cost is extremely high; and, consequently, their availability is quite restricted.

Our interest has, therefore, been to synthesize novel compounds structurally related to the natural prostaglandins but with the following unique advantages; (a) simplicity of synthesis leading to low cost of production; (b) specificity of biological activity which may be either of a prostaglandin-mimicking or prostaglandin-antagonizing type; (c) enhanced metabolic stability. The combination of these advantages serves to provide effective, orally and parenterally active therapeutic agents for the treatment of a variety of human and animal diseases. Included are applications in renal, cardiovascular, gastrointestinal, respiratory, immune, and reproductive systems, and in the control of lipid metabolism, inflammation, blood clotting, skin diseases, and certain autoimmune diseases.

More specifically, in the clinic, prostaglandin agonists can function as agents for improving renal function (e.g., renal vasodilation), anti-ulcer agents, agents for fertility control, antithrombotics, antiasthmatics, antilipolytics, antineoplastic agents, agents for the treatment of certain skin diseases, dwarfism (by inducing growth hormone release) and certain autoimmune diseases.

Prostaglandin antagonists can function as antiinflammatory agents, anti-diarrheal agents, antipyretics, agents for prevention of premature labor, and agents for the treatment of headache.

The compounds of the present invention are useful as pharmaceutically active compounds. Thus, these compounds are orally active in the treatment of conditions which are responsive to the actions of the natural prostaglandins. It is of course necessary to determine by routine laboratory testing which of the compounds of the present invention are most suitable for a specific end use. Some of the compounds of the invention have prostaglandin-like activity in that they mimic the effect of prostaglandin $E_1$ in stimulating the formation of cyclic AMP in the mouse ovary in vitro.

Certain of the compounds of this invention, e.g., 7-[N-(4-hydroxynonyl)methanesulfonamido]heptanoic acid and 4-[N-(4-hydroxynonyl)methanesulfonamido]butoxyacetic acid, mimic the effects of prostaglandin $E_1$ and thus are useful on oral administration in producing increased renal blood flow in laboratory animals and are useful in improving renal function in animals with poorly-functioning kidneys.

Also, certain of the compounds of this invention are effective in inhibiting the aggregation of platelets in blood stimulated with collagen to cause platelet aggregation, and thus, in inhibiting platelet aggregation, are useful in preventing thrombus formation. An example of two of these compounds are 7-[N-(4-hydroxynonyl)-methanesulfonamido]heptanoic acid and 4-[N-(4-hydroxynonyl)methanesulfonamido]butoxyacetic acid.

The compounds of this invention are also indicated to be useful in therapy as regulators of the immune response. The basis for their activity in this area is their ability to stimulate cyclic-AMP formation in cells. Agents, including the E prostaglandins, that increase cellular cyclic-AMP concentration, interfere with the cell-mediated immune response by inhibiting lymphocyte expression in response to antigen, by inhibiting release of pathological mediators from sensitized lymphocytes, and by inhibiting the killing of target cells by such lymphocytes. Various assays which depend upon the measurement of some function of the immunologically competent lymphocyte can be used to demonstrate that the prostaglandin analogs of this invention are similarly active. For example, the release of lymphokines (proteins that are agents of inflammation and tissue destruction) from sensitized lymphocytes in culture is strongly inhibited by these analogs in low concentrations. Thus, it is apparent that the compounds of this invention are applicable to the treatment of those autoimmune diseases in whose pathogenesis a cell-mediated immune reaction is involved. Such diseases range from contact dermatitis to such chronic destructive diseases as rheumatoid arthritis and possibly multiple sclerosis and systemic lupus erythematosus.

The present prostaglandin analogs are also effective in preventing the rejection of transplanted organs. The biochemical basis for this action is the same as outlined in the preceding paragraph, for the rejection of organ grafts is considered to be predominantly a cell-mediated immune phenomenon and the hallmark of organ rejection is the infiltration of cytotoxic lymphocytes into the graft. Direct evidence that the compounds of this invention can retard or prevent transplant rejection has been obtained in the rat renal allograft model; in this system, administration of the compounds of the present invention prevents the rejection of the transplanted kidney and the subsequent death of the host rat, which events invariably occur in the cases of untreated rats of those treated with the immunosuppressants. An example of a compound of this invention which possesses immunoregulant activity of the kind discussed in this paragraph and the one above is 7-[N-(4-hydroxynonyl)methanesulfonamido]-heptanoic acid.

Because of their biological activity and ready accessibility, the compounds of the invention are also useful in that they permit large-scale animal testing useful and necessary to understanding of these various disease conditions such as kidney impairment, ulcers, dwarfism caused by poorly-functioning pituitary glands, stroke (thrombus formation), and the like. It will be appreciated that not all of the compounds of this invention have these biological activities to the same degree, but the choice of any particular ones for any given purpose will depend upon several factors including the disease to be treated.

The compounds of this invention are particularly useful for improving renal function in that they are renal vasodilators and effect increased blood flow in laboratory animals, for preventing thrombus formation, and for stimulating the release of growth hormone in animals with poorly-functioning pituitary glands.

The compounds of this invention can be administered either topically or systemically, i.e., intravenously, subcutaneously, intramuscularly, orally, rectally, or by aerosolization in the form of sterile implants for long action. They can be formulated in any of a number of pharmaceutical compositions and non-toxic carriers to this end.

The pharmaceutical compositions can be sterile injectable suspensions or solutions, or solid orally administrable pharmaceutically acceptable tablets or capsules; the compositions can also be intended for sublingual administration, topical application, or for suppository use. It is especially advantageous to formulate compositions in dosage unit forms for ease and economy of administration uniformity of dosage. "Dosage unit form" as a term used herein refers to physically discrete units suitable as unitary dosages for animal and human subjects, each unit containing a predetermined quantity of active material calculated to produce the desired biological effect in association with the required pharmaceutical means. Illustratively, a sterile injectable composition can be in the form of aqueous or oleagenous suspensions or solutions.

The sterile injectable composition can be aqueous or oleagenous suspension or solution. Solutions are similarly prepared from the salt form of the compound. For the laboratory animals, we prefer to use incomplete Freund's adjuvant or sterile saline (9%) as carrier. For human parenteral use, such as intramuscularly, intravenously, or by regional perfusion, the diluent can be a sterile aqueous vehicle containing a preservative, for example, methylparaben, propylparaben, phenol, and chlorobutanol. The aqueous vehicle can also contain sodium chloride, preferably in an amount to be isotonic, as well as a suspending agent, for example, gum arabic, polyvinylpyrrolidone, methylcellulose, acetylated monoglyceride (available commercially as Myvacet from Distillation Products Industry, a division of Eastman Kodak Company), monomethyl glyceride, dimethyl glyceride, Emulphor (available from Badische Anilin Sodafabrik), or a moderately high molecular weight polysorbitan (commercially available under the tradenames Tween or Span from Atlas Powder Company, Wilmington, Delaware). Other materials employed in the preparation of chemotherapeutic compositions containing the compound may include glutathione, 1,2-propanediol, glycerol, and glucose. Additionally, the pH of the composition is adjusted by use of an aqueous solution such as tris(hydroxymethyl)aminomethane (tris buffer).

Oily pharmaceutical carriers can also be used, since they dissolve the compound and permit high doses. Many oily carriers are commonly employed in pharmaceutical use, such as, for example, mineral oil, lard, cottonseed oil, peanut oil, sesame oil, or the like.

It is preferred to prepare the compositions, whether aqueous or oils, in a concentration in the range of from 2–50 mg./ml. Lower concentrations require needless quantities of liquid. Higher concentrations than 50 mg./ml. are difficult to maintain and are preferably avoided.

Oral administration forms of the drug can also be prepared for laboratory animals or human patients provided that they are encapsulated for delivery in the gut. The drug is subject to enzymatic breakdown in the acid environment of the stomach. The same dosage levels can be used as for injectable forms; however, even higher levels can be used to compensate for biodegradation in the transport. Generally, a solid unit dosage form can be prepared containing from 0.5 mg. to 25 mg. active ingredient.

Whatever the mode of administration, doses in the range of about 0.10 to 20 mg./kg. of body weight administered one to four times per day are used. The exact dose depending on the age, weight, and condition of the patient, and the frequency and route of administration.

The low cost and ready accessibility of the compounds of this invention make them particularly promising for applications in veterinary medicine in which field their utilities are comparable to those in human medicine.

PROCESSES TO PREPARE THE COMPOUNDS OF THIS INVENTION:

The new chemical compounds with which this invention is concerned are prepared by the following two processes. The first process involves the reaction of a compound such as III with a compound such as IV, wherein A, $y$, Z, $R^1$, $R^2$, $R^4$ and $R^5$ are as defined:

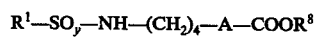

III

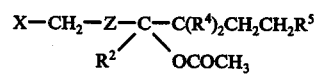

IV

IV as in formula I above and $R^8$ is loweralkyl having 1–5 carbon atoms, preferably ethyl; and X is halogen, e.g., chloro, bromo, or iodo. The reaction is carried out by preparing the alkali metal salt of III by reaction of III with sodium hydride in a solvent, such as a 1:1 mixture of benzene and dimethylformamide, adding compound IV at ambient temperature, then heating the reaction mixture at 50°–100° C. for from one to twenty hours. This reaction scheme affords intermediates represented by formula V:

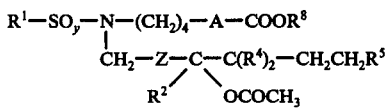

Mild basic hydrolysis (NaOH in aqueous methanol or ethanol) of the ester functions of compound V affords compounds of formula I, e.g., VI:

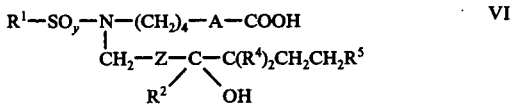

In the second process a compound such as VII is caused to react with a compound of formula VIII, wherein A, X, y, Z, $R^1$, $R^4$, and $R^8$ are as defined as in formulas III and IV above, and THP is the 2-tetrahydropyranyl group. The reaction is carried

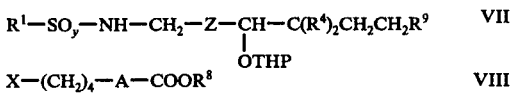

out by preparing the alkali metal salt of VII (wherein $R^9$ is hydrogen, loweralkyl of 1-4 carbon atoms, or 2,2,2-trifluoroethyl) by reaction of VII with sodium hydride in a solvent such as 1:1 mixture of benzene and dimethylformamide, adding compound VIII at ambient temperature then heating the reaction at 50°-100° C. for from 1-20 hours. This reaction scheme affords intermediates represented by formula IX:

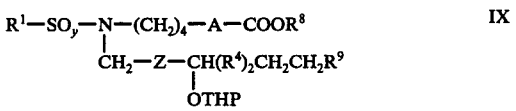

Mild acid hydrolysis (aqueous HCl in methanol or ethanol) removes the tetrahydropyranyl protecting group, then mild basic hydrolysis (NaOH in aqueous methanol or ethanol) of the ester function affords compounds of formula I, e.g., X:

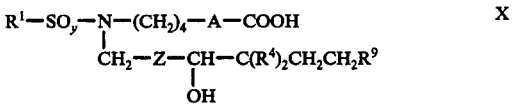

It is frequently advantageous from a therapeutic standpoint to prepare compounds of this invention (formula I) in which the asymmetric carbon atom which bears $OR^3$ is exclusively in the R or S configuration.

The compounds of the instant invention in which the $C_{12}$-carbon is in the S-configuration have greater biological activity than those in which the $C_{12}$-carbon is in the R-configuration. The relative biopotency is readily determined in any particular instance by the use of the in vitro or in vivo assays referred to hereinabove.

In our series of 8-aza-9-oxo(and dioxo)thia-11,12-secoprostaglandins, compounds which are exclusively R or S at this center can be produced by employing preresolved compounds IV or VII and carrying out the steps of process 1 or 2. An example of the use of such a preresolved compound IV is given under the section "Preparation of Intermediates" (Examples J and K).

DERIVATIZATION OF PRODUCTS

The directly obtained products of the processes described supra can be derivatized to yield the other products of formula I.

1. The fundamental processes yield compounds where R is carboxy. To obtain carboxy salts the acid products are dissolved in a solvent such as ethanol, methanol, glyme and the like and the solution treated with an appropriate alkali or alkaline earth hydroxide or alkoxide to yield the metal salt, or with an equivalent quantity of ammonia, amine or quaternary ammonium hydroxide to yield the amine salt. In each instance, the salt either separates from the solution and may be separated by filtration or, when the salt is soluble it may be recovered by evaporation of the solvent. Aqueous solutions of the carboxylic acid salts can be prepared by treating an aqueous suspension of the carboxylic acid with an equivalent amount of an alkaline earth hydroxide or oxide, alkali metal hydroxide, carbonate or bicarbonate, ammonia, an amine or a quaternary ammonium hydroxide.

To obtain carboxy esters (i.e., compounds where R is alkoxycarbonyl) the acid products are treated in ether with an ethereal solution of the appropriate diazoalkane. For example, methyl esters are produced by reaction of the acid products with diazomethane. To obtain products where R is carbamoyl or substituted carbamoyl, the acid product is first converted to an active Woodward ester. For example, the acid product can be made to react with N-tert-butyl-5-methylisoxazolium perchlorate in acetonitrile in the presence of a base such as triethylamine to yield an active ester in which R is

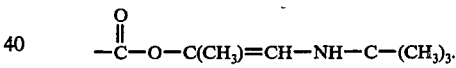

Active esters of this type can be reacted with ammonia to yield products of formula I where R is carbamoyl, with primary or secondary amines or di-loweralkylaminoalkylamines to yield products where R is substituted carbamoyl, i.e., $-CONR^6R^7$, and with hydrazine to yield products wherein R is carbazoyl.

2. The fundamental process yields products where $R^3$ is hydrogen. In compounds of formulas VI and X, reaction with formic acid, acetic anhydride, propionic anhydride, butyric anhydride, isobutyric anhydride, valeric anhydride, pivalic anhydride, and the like, without solvent and at temperatures from 25° to 60° C., gives compounds wherein $R^3$ is formyl, acetyl, propionyl, butyryl, isobutyryl, valeryl, and pivaloyl, respectively.

PREPARATION OF STARTING MATERIALS

1. The reagent III which has the general formula shown, wherein A, Y, $R^1$, and $R^8$ are as defined previously, is prepared in the following manner. The sodium salt of the corresponding alkanesulfonamide or alkanesulfinamide is treated with the appropriate halo compound (i.e., $X-(CH_2)_4-A-COOR^8$) to give reagent III:

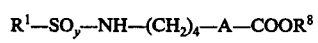

The reagent IV A which has the following general formula wherein X is halogen and $R^5$ and $R^4$ are as previously

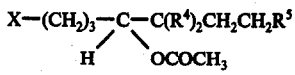   IV A defined as prepared in the following manner. A Grignard reagent $R^5CH_2CH_2(R^4)_2C$—MgI or $R^5CH_2CH_2(R^4)_2C$—MgBr is allowed to react, in ether, with a nitrile $X(CH_2)_3CN$. The resulting imine is hydrolyzed in aqueous acidic solution to give ketones of the formula XI:

$X(CH_2)_3C(=O)C(R^4)_2CH_2CH_2R^5$   XI

The ketones (XI) are reduced to the corresponding alcohols $X(CH_2)_3CH(OH)$—$C(R^4)_2CH_2CH_2R^5$ with sodium or potassium borohydride in a suitable solvent such as methanol, ethanol, or diglyme. Acetylation of these alcohols, preferably with acetic anhydride, yields the reagents IV A.

By treatment of ketone XI with Grignard reagents $R^2$MgBr(or I) where $R^2$ is methyl, ethyl or propyl, compounds of formula $X(CH_2)_3C(R^2)(OH)C(R^4)_2CH_2CH_2R^5$ are obtained which upon acetylation with acetic anhydride in pyridine give compounds of formula IV B:

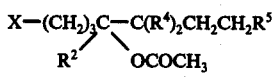   IV B

The reagents IV C which have the following general formula

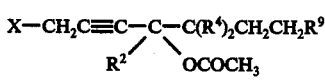   IV C wherein X, $R^2$ and $R^4$ are as defined previously and $R^9$ is hydrogen, loweralkyl of 1–4 carbon atoms or 2,2,2-trifluoroethyl are prepared in the following manner. Acetylenic alcohols $HC≡C—C(R^2)(OH)C(R^4)_2CH_2CH_2R^9$ are treated with acetic anhydride to give the acetylated alcohols $HC≡C—C(R^2)(OCOCH_3)C(R^4)_2CH_2CH_2R^9$. Those compounds are treated with paraformaldehyde and diethylamine to afford the tertiary amines $(C_2H_5)_2N—CH_2C≡C—C(R^2)(OCOCH_3)C(R^4)_2CH_2CH_2R^9$ which when treated with cyanogen halide, e.g, bromide yield the reagents IV C. The acetylenic alcohols $HC≡C—C(R^2)—(OH)—C(R^4)_2CH_2CH_2R^9$ intermediates for compounds of formula IV C are prepared by reaction of ethynylmagnesium bromide or lithium acetylide with aldehydes or ketones of the formula $R^9CH_2CH_2C(R^4)_2C(R^2)=O$.

By using the resolved R and S forms of the $HC≡C—CH(OH)C(R^4)_2CH_2CH_2R^9$ in the above scheme, the corresponding R and S forms of the reagent IV C can be obtained.

It should be noted here that the use of the R or S enantiomers of reagent IV C produce the R and S enantiomers, respectively, of compounds of formula VI A wherein $R^1$, $R^2$, $R^4$, $R^9$, and Y are as defined previously and $Z^1$ is —C≡C—.

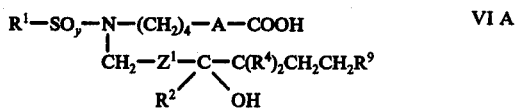   VI A

These optically active products VI A can be hydrogenated over a platinum catalyst to give the R and S enantiomers of compounds of formula VI A where Z is ethylene —$CH_2$—$CH_2$—.

The reagent IV D which has the following general formula:

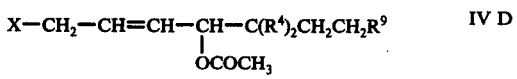   IV D wherein X, $R^4$ and $R^9$ are as defined above and are prepared in the following manner. A Grignard reagent $R^9CH_2CH_2C(R^4)_2$—MgBr or $R^9CH_2CH_2C(R^4)_2$MgI is allowed to react with crotonaldehyde to give, after hydrolysis, the alcohol $CH_3CH=CH—CH(OH)—C(R^4)_2CH_2CH_2R^9$. This alcohol is acetylated, preferably with acetic anhydride without solvent at 30°–100° C. for 2–12 hours, to give the intermediate $CH_3CH=CH—CH(OCOCH_3)—C(R^4)_2CH_2CH_2R^9$.

This intermediate is allowed to react with N-bromosuccinimide in carbon tetrachloride at 50–70° C. for 2.5 to 5 hours to effect allylic bromination and give the reagent of formula IV D.

3. The reagent VII which has the formula shown is prepared by the following reactions. The alcohol prepared

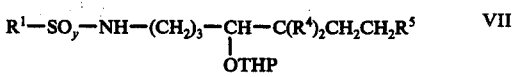   VII in Section 2 above with the formula

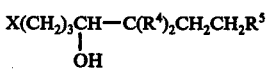

is treated with dihydropyran and a catalytic amount of acid to give

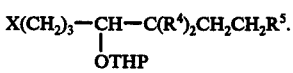

Treatment of this halo compound with the sodium salt of phthalimide in dimethylformamide affords the corresponding phthalimido compound. Cleavage of this compound with hydrazine in ethanol yields the amine

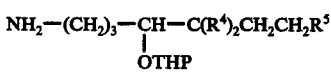

which upon treatment with the appropriate alkanesulfonyl chloride or alkanesulfinyl chloride in pyridine affords the reagent VII.

4. The preparation of reagents of formula VIII has been described in the scientific and patent literature in instances

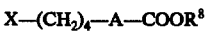   VIII where A is ethylene, trimethylene, α-methylethylene, β-methylethylene, α,α-dimethylethylene, β, β-dimethylethylene. To prepare reagents where A is oxymethylene, an ester of glycolic acid, $HOCH_2COOR^8$ is treated with a strong base, preferably sodium hydride, in a non-protic solvent (dimethylformamide, glyme, and the like) and the resulting anion caused to react with a 1,4-dihalobutane, preferably 1,4-dibromobutane. The glycolic ester and base are employed in approximately equimolar quantities; a 1.5 to 2 molar excess of the dihalobutane is advantageously used.

5. Methods for obtaining optical antipodes of some compounds of this invention have been described supra whereby one of the compounds of the molecule is preresolved prior to its assembly into the whole molecule. Other methods also can be employed; for example, mixtures of racemates may be separated by taking advantage of the physiochemical difference between the components using chromatography and/or fractional crystallization. The racemic products and intermediates of this invention can be resolved into their optically active components by any one of a number of methods of resolution which are well described in the chemical literature.

Those compounds which are carboxylic acids can be converted to the diastereoisomeric salts by treatment with an optically active base such as + or − α-methylbenzylamine, + or − α-(1-naphthyl)-ethylamine, brucine, cinchonine, cinchonidine, or quinine. These diastereoisomeric salts can be separated by fractional crystallization.

The carboxylic acids of this invention also can be converted to esters using an optically active alcohol, such as, estradiol-3-acetate, or d- or l-menthol and the diastereoisomeric esters resolved by crystallization or by chromatographic separation.

Racemic carboxylic acids also may be resolved by reverse phase and absorption chromatography using an optically active support and absorbent.

Compounds of this invention which contain free hydroxyl groups can be esterified with acid chlorides or anhydrides derived from optically active acids, such as, (=)-10-camphorsulfonic acid, (=)-α-bromocamphor-τ-sulfonic acid, or d- or 1-6,6'-dinitrodiphenic acid to form esters which can be resolved by crystallization.

Another method of obtaining pure optical isomers involves incubation of the racemic mixture with certain microorganisms such as fungi, by processes well established in the art, and recovering the product formed by the enzymatic transformation.

The methods described supra are especially effective if one applies the process to a compound where one asymmetric center has been preresolved by the techniques already described.

This invention is further described in the following examples.

PREPARATION OF INTERMEDIATES

A. Preparation of 1-Chloro-4-acetoxynonane

Step 1. Preparation of 1-Chloro-4-nonanone

To the Grignard reagent prepared from a mixture of amyl bromide (226.59 g.; 1.5 moles) and magnesium (36.48 g.; 1.5 moles) in ether (100 ml.) is added, dropwise, during one hour, 4-chlorobutyronitrile (155.34 g.; 1.5 moles). Stirring is continued for an additional one hour. The reaction mixture is poured into a mixture of finely crushed ice (1000 g.) and concentrated hydrochloric acid (750 ml.). The ether layer is separated quickly and discarded. The aqueous layer is heated on a steam bath for one hour to hydrolyze the intermediate imine and cause the separation of the ketone as an oil. After cooling, the oil is extracted with ether and the combined extracts are washed with saturated sodium chloride solution and dried over anhydrous sodium sulfate. The solvent is removed under vacuum and the residual oil is distilled to give 69.0 g. (26%) of colorless oil, b.p. 115°–117° /14 mm.; pmr (CDCl₃) δ 0.90 (3H,t), 3.56 (2H,t,CH₂Cl).

Step 2. Preparation of 1-Chloro-4-nonanol

A suspension of sodium borohydride (6.62 g.; 0.175 mole) and sodium hydroxide (1.3 g.) in ethanol (310 ml.) is treated, dropwise, over 1 hour with 1-chloro-4-nonanone (61.40 g.; 0.349 mole) while the temperature is maintained at 45°–50° C. Stirring is continued for one hour, longer without external cooling.

The reaction mixture is acidified with concentrated hydrochloric acid to the Congo red endpoint and then the ethanol is removed under reduced pressure. The residue is treated with water (200 ml.) and the resulting oil is extracted with ether. The combined extracts are washed with saturated sodium chloride solution and dried over anhydrous sodium sulfate. The solvent is removed under vacuum to give the title compound as a light yellow residual oil, yield 58.85 g.; ir (neat) 3400 cm⁻¹.

Step 3. Preparation of 1-Chloro-4-acetoxynonane

A mixture of 1-chloro-4-nonanol (111.99 g.; 0.627 mole) and acetic anhydride (128.0 g.; 1.254 moles) is heated on a steam bath for 1½ hours.

The volatile materials are removed under reduced pressure and the residual oil is distilled to give 88.6 g. (64%) of colorless oil, b.p. 130–133° /14 mm.; pmr (CDCl₃) δ 0.89 (3H,t), 2.02 (3H,s CH₃COO), 3.53 (2H,t CH₂Cl), 4.89 (1H,m). Anal. Calcd. for $C_{11}H_{21}ClO_2$: C, 59.85; H, 9.59 Found: C, 59.87; H, 9.67.

B. Preparation of 1-Chloro-4-acetoxy-8-methylnonane

Step 1. Preparation of 1-Chloro-8-methyl-4-nonanone

To the Grignard reagent prepared from a mixture of 1-bromo-4-methylpentane (200.00 g.; 1.21 mole) and magnesium (29.43 g.; 1.21 mole) in ether (800 ml.) is added, dropwise during one hour, 4-chlorobutyronitrile (125.30 g.; 1.21 mole). Stirring is continued for an additional one hour.

The reaction mixture is poured into a mixture of finely crushed ice (800 g.) and concentrated hydrochloric acid (600 ml.). The ether layer is separated quickly and discarded. The aqueous layer is heated on a steam bath for one hour to hydrolyze the intermediate imine and cause the separation of the ketone as an oil. After cooling, the oil is extracted with ether and the combined extracts are washed with saturated sodium chloride solution and dried over anhydrous sodium sulfate. The solvent is removed under vacuum and the residual oil is distilled to give 23.3 g. (10%) of colorless oil, b.p. 121°–122° /15 mm.; pmr (CDCl₃) δ 0.89 (6H,d), 3.57 (2H,t CH₂Cl).

Anal. Calcd. for $C_{10}H_{19}ClO$; C, 62.98; H, 10.04

Found: C, 62.86; H, 10.20

Step 2. Preparation of 1-Chloro-8-methyl-4-nonanol

A suspension of sodium borohydride (2.3 g., 0.061 mole) and sodium hydroxide (0.5 g.) in ethanol (110 ml.) is treated dropwise during one hour with 1-chloro-8-methyl-4-nonanone (23.0 g., 0.121 mole) while the temperature is maintained at 45°–50° LC. Stirring is continued for one hour longer without external cooling.

The reaction mixture is acidified with concentrated hydrochloric acid to the Congo Red endpoint and then the ethanol is removed under reduced pressure. The residue is treated with water (70 ml.) and the resulting oil is extracted with ether. The combined extracts are washed with saturated sodium chloride solution and dried over anhydrous sodium sulfate. The solvent is removed under vacuum to give the title compound as a light yellow residual oil, yield 22.73 g.; ir (neat) 3400 cm$^{-1}$.

Step 3. Preparation of 1-Chloro-4-acetoxy-8-methylnonane

A mixture of 1-chloro-8-methyl-4-nonanol (22.73 g.; 0.118 mole) and acetic anhydride (24.07 g.; 0.236 mole) is heated on a steam bath for 1½ hours.

The volatile materials are removed under reduced pressure and the residual oil is distilled to give 14.58 g. (58%) of colorless oil, b.p. 138°–139°/15 mm.; pmr (CDCl$_3$) δ 0.85 (6H,d), 2.02 (3H,s CH$_3$COO), 3.53 (2H,t CH$_2$Cl), 4.92 (1H,m).

C. Preparation of 1-Chloro-4-acetoxyundecane

Step 1. Preparation of 1-Chloro-4-undecanone

This compound is prepared essentially by the same procedure as described for 1-chloro-4-nonanone (Example A, Step 1) using the following reagents:

| | |
|---|---|
| 1-Bromoheptane | 214.94 g. (1.2 mole) |
| Magnesium | 29.18 g. (1.2 mole) |
| Ether | 800 ml. |
| 4-Chlorobutyronitrile | 124.27 g. (1.2 mole) |

The title compound is obtained as a colorless oil, yield 60.4 g. (15%), b.p. 135°–140°/15 mm.; pmr (CDCl$_3$) δ 0.93, (3H,t), 3.57 (2H,t CH$_2$Cl).

Step 2. Preparation of 1-Chloro-4-undecanol

This compound is prepared essentially by the same procedure as described for 1-chloro-4-nonanol (Example A, Step 2) using the following reagents:

| | |
|---|---|
| Sodium borohydride | 5.56 g. (0.147 mole) |
| Sodium hydroxide | 1.12 g. |
| Ethanol | 265 ml. |
| 1-Chloro-4-undecanone | 60.00 g. (0.294 mole) |

The title compound is obtained as a yellow residual oil, yield 60.02 g.

Step 3. Preparation of 1-Chloro-4-acetoxyundecane

This compound is prepared essentially by the same procedure as described for 1-chloro-4-acetoxy-nonane (Example A, Step 3), using the following reagents:

| | |
|---|---|
| 1-Chloro-4-undecanol | 60.02 g. (0.29 mole) |
| Acetic anhydride | 59.16 g. (0.58 mole) |

The title compound is obtained as a colorless oil, yield 44.6 g. (62%), b.p. 155°–158°/15 mm.; pmr (CDCl$_3$) δ 0.88 (3H,t), 2.02 (3H,s CH$_3$COO), 3.53 (2H,t CH$_2$Cl), 4.92 (1H,m).

Anal. Calcd. for C$_{13}$H$_{25}$ClO$_2$: C, 62.76; H, 10.13 Found: C, 63.03; H, 10.40

D. Preparation of 1-Chloro-4-acetoxy-8,8-dimethyl-nonane

By following the procedure described for 1-chloro-4-acetoxynonane (Example A) but substituting 1-bromo-4,4-dimethylpentane for amyl bromide, there is obtained in succession: 1-chloro-8,8-dimethyl-4-nonanone, 1-chloro-8,8-dimethyl-4-nonanol, and 1-chloro-4-acetoxy-8,8-dimethylnonane.

E. Preparation of 1-Chloro-4-acetoxy-9,9,9-trifluorononane

By following the procedure described for 1-chloro-4-acetoxynonane (Example A) but substituting 1-bromo-5,5,5-trifluoropentane for amyl bromide, there is obtained in succession: 1-chloro-9,9,9-trifluoro-4-nonanone, 1-chloro-9,9,9-trifluoro-4-nonanol, and 1-chloro-4-acetoxy-9,9,9-trifluoronane.

F. Preparation of 1-Chloro-4-acetoxy-8-nonene

By following the procedure described for 1-chloro-4-acetoxynonane (Example A) but substituting 1-bromo-4-pentene for amyl bromide, there is obtained in succession: 1-chloro-8-nonen-4-one, 1-chloro-8-nonen-4-ol, and 1-chloro-4-acetoxy-8-nonene.

G. Preparation of 1-Chloro-4-acetoxy-5,5-dimethylnonane

Step 1. Preparation of 1-Chloro-5,5-dimethyl-4-nonanone

Four hundred ml. of a solution in ether of 1,1-dimethylpentylmagnesium chloride prepared from magnesium (24.3 g., 1.0 mole) and 1-chloro-1,1-dimethylpentane (134.5 g., 1.0 mole) according to the procedure of Whitmore and Badertscher [J. Am. Chem. Soc., 55, 1559 (1933)] is added dropwise with stirring to 4-chloro-butyryl chloride (197 g., 1.4 moles) in ether (400 ml.) during 6 hours. The reaction mixture is stirred for an additional 12 hours. It is then poured into a mixture of ice and dilute hydrochloric acid. The ether layer is separated, washed with water and brine and dried over sodium sulfate. The ether is evaporated and the residue distilled at aspirator vacuum through a Vigreaux column to yield the product as a colorless oil.

Step 2. Preparation of 1-Chloro-5,5-dimethyl-4-nonanol

By following the procedure described for 1-chloro-4-nonanol (Example A, Step B) but substituting 1-chloro-5,5-dimethyl-4-nonanone for 1-chloro-4-nonanone and continuing stirring and heating at 50° for 6 hours, there is obtained 1-chloro-5,5-dimethyl-4-nonanol.

Step 3. Preparation of 1-Chloro-4-acetoxy-5,5-dimethylnonane

By following the procedure described for 1-chloro-4-acetoxynonane (Example A, Step 3) but substituting 1-chloro-5,5-dimethyl-4-nonanol for 1-chloro-4-nonanol and continuing the steam bath heating for 4 hours, there is obtained 1-chloro-4-acetoxy-5,5-dimethylnonane.

H. Preparation of 1-Bromo-4-acetoxy-2-nonene

A mixture of 4-acetoxy-2-nonene (73.5 g., 0.4 mole), N-bromosuccinimide (80.0 g., 0.45 mole), and carbon tetrachloride (500 ml.) is boiled under reflux for 3 hours. The mixture is then cooled and the suspended succinimide, removed by filtration. The carbon tetrachloride solution is washed with dilute sodium bicarbonate solution and water, and is dried over sodium sulfate. The carbon tetrachloride is evaporated in vacuo and the residual oil is distilled to yield 62 g. (59%) of 1-bromo-4-acetoxy-2-nonene as a light yellow oil, b.p. 110°–112°/0.1 mm.

I. Preparation of 1-Bromo-4-acetoxy-2-nonyne

Step 1. Preparation of 3-Acetoxy-1-octyne

1-Octyn-3-ol (100 g., 0.794 mole) is dissolved in pyridine (79 g., 1.0 mole) and acetic anhydride 81.6 g., 0.80 mole) is added dropwise with stirring during one hour. The temperature rises to 45°. The solution is heated at 55° for one hour and is then cooled and poured into 200 ml., ice-cold 5% hydrochloric acid. The oily product is taken up in ether, washed with water and brine and dried over sodium sulfate. The ether is evaporated and the residual oil distilled to yield 106.4 g. (80%) of 3-acetoxy-1-octyne, b.p. 91°–92°/15 mm.

Step 2. Preparation of 1-Diethylamino-4-acetoxy-2-nonyne

A mixture of 3-acetoxy-1-octyne (58.8 g., 0.35 mole), diethylamine (28.5 g., 0.39 mole), paraformaldehyde (13.8 g., 0.46 mole) and p-dioxane (60 ml.) is heated on the steam bath under a reflux condenser for 17 hours. The resulting solution is cooled and diluted with 250 ml. of ether. The solution is extracted with 300 ml. of 5% hydrochloric acid. The acidic aqueous extract is made basic with 10% sodium hydroxide solution. The liberated amine is taken up in ether, washed with water and brine and dried over sodium sulfate. The ether is evaporated and the residual oil distilled to yield 73.1 g. (89%) of 1-diethylamino-4-acetoxy-2-nonyne, b.p. 103°–109°/0.3 mm.

Anal. calcd. for $C_{15}H_{27}NO_2$: C, 71.10; H, 10.74; N, 5.33 Found: C, 70.73; H, 11.03; N, 5.55

Step 3. Preparation of 1-Bromo-4-acetoxy-2-nonyne

A solution of 1-diethylamino-4-acetoxy-2-nonyne (50.6 g., 0.20 mole) and cyanogen bromide (21.2 g., 0.20 mole) in ether (250 ml.) is allowed to stand at 25°–27° for 18 hours. The ether solution is washed with 5% hydrochloric acid solution, water, and brine and dried over sodium sulfate. The ether is evaporated and the residual oil distilled. After a forerun of diethylcyanamide, there is collected 34.1 g. (65%) of 1-bromo-4-acetoxy-2-nonyne, b.p. 97°–105°/0.2 mm.

Anal. calcd. for $C_{11}H_{17}BrO_2$: C, 50.59; H, 6.56 Found: C, 50.54; H, 6.49

J. Preparation of 1-Bromo-4(R)-acetoxy-2-nonyne

By following the procedure described in Example H but substituting (R)-1-octyn-3-ol $[\alpha]_D^{26}$ + 6.1° [C 3.1, CHCl$_3$] for the racemic 1-octyn-3-ol, there is obtained successively: 3(R)-acetoxy-1-octyne, $[\alpha]_D^{26}$ + 70° [C 3.1, CHCl$_3$], 1-diethylamino-4(R)-acetoxy-2-nonyne, $[\alpha]_D^{26}$ + 74° [C 3.2, CHCl$_3$], and 1-bromo-4(R)-acetoxy-2-nonyne, $[\alpha]_D^{26}$ + 75° [C 3.2, CHCl$_3$].

K. Preparation of 1-Bromo-4(S)-acetoxy-2-nonyne

By following the procedure described in Example H but substituting (S)-1-octyn-3-ol, $[\alpha]_D^{26}$ − 6.4° [C 3.3, CHCl$_3$], for the racemic 1-octyn-3-ol, there are obtained successively: 3(S)-acetoxy-1-octyne, $[\alpha]_D^{26}$ − 79° [C 3.0, CHCl$_3$], 1-diethylamino-4(S)-acetoxy-2-nonyne, $[\alpha]_D^{26}$ − 80° [C 3.3, CHCl$_3$], and 1-bromo-4(S)-acetoxy-2-nonyne, $[\alpha]_D^{26}$ − 83° [3.7, CHCl$_3$].

L. Preparation of Methyl 7-bromo-2-methylheptanoate

Step 1. Preparation of 5-Acetoxypentyl chloride

Acetic anhydride (102 g., 1 mole) is added dropwise with stirring to pentamethylene chlorohydrin (90 g., 0.74 mole). The resulting solution is heated on the steam bath for one hour and allowed to stand overnight at room temperature. The reaction mixture is distilled to yield 83.6 g. (69%) of 5-acetoxypentyl chloride, b.p. 101°–104°/20 mm.

Step 2. Preparation of Diethyl (5-Acetoxypentyl)methylmalonate

Sodium hydride (4.8 g., 0.2 mole) as a 50% suspension in mineral oil is washed with petroleum ether under nitrogen to remove the mineral oil, suspended in dry benzene (150 ml.), and the suspension cooled in an ice bath. Diethyl methylmalonate (34.8 g., 0.2 mole) dissolved in sieve dried DMF (150 ml.) is added to the suspension of sodium hydride dropwise. The mixture is allowed to stand overnight at room temperature. Potassium iodide (0.4 g.) and 5-acetoxyphenyl chloride (32.9 g., 0.2 mole) are then added, and the mixture is heated for 24 hours at 125° in an oil bath. The reaction mixture is concentrated in vacuo, diluted with ether (200 ml.), and filtered to remove sodium chloride. The filtrate is washed with brine, dried over anhydrous magnesium sulfate and concentrated to yield 39.6 g. (66%) of oily product.

Step 3. Preparation of 7-Bromo-2-methyl-heptanoic acid

A mixture of the crude diethyl (5-acetoxypentyl)methylmalonate (68 g., 0.23 mole) and 48% aqueous hydrobromic acid (100 ml.) is refluxed for 20 hours. The mixture is then concentrated by distillation until the internal temperature rises to 120°; 96 ml. of distillate (2 layers) is collected. The residual liquid is cooled, dissolved in ether, washed with brine, dried over magnesium sulfate, and the solution concentrated in vacuo to yield 54 g. of crude 7-bromo-2-methylheptanoic acid as a dark viscous liquid.

Step 4. Preparation of Methyl 7-Bromo-2-methylheptanoate

A solution of crude 7-bromo-2-methylheptanoic acid (54 g., 0.24 mole) and concentrated sulfuric acid (2 drops) in absolute methanol (300 ml.) is refluxed for 5 hours. After standing overnight at room temperature, the solution is concentrated in vacuo and diluted with water. The mixture is made basic by the addition of saturated sodium carbonate solution and the product taken up in ether. The ether extract is washed with water, dried over anhydrous magnesium sulfate and distilled to yield 11.8 g. (16%) of methyl 7-bromo-2-methylheptanoate, b.p. 67°–70°/0.05 mm.; pmr (CDCl$_3$) δ 1.13 (3H,d 2-CH$_3$), 2.42 (1H,m CHCOOCH$_3$), 3.38 (2H,t CH$_2$Br), 3.65 (3H,s CH$_3$O).

M. Preparation of Ethyl 4-Bromobutoxyacetate

Sodium hydride (9.0 g., 0.375 mole) is suspended in 1,2-dimethoxyethane. The mixture is stirred and cooled in an ice bath while ethyl glycollate (39.0 g., 0.375 mole) is added dropwise during one hour. 1,4-Dibromobutane (108 g., 0.5 mole) is added all at once to the resulting thick suspension. The mixture is warmed gently to initiate a strongly exothermic reaction; then the mixture is heated 3 hours on the steam bath. The mixture is poured into cold water. The heavy oil layer is taken up in ether, washed with three portions of water, and dried over sodium sulfate.

Evaporation of the ether and distillation of the residual oil yields 21.3 g. (24%) of ethyl 4-bromobutoxyacetate, a colorless oil, b.p. 99°–103°/0.2 mm.

N. Preparation of N-[4-(2-Tetrahydropyranyloxy)nonyl]-methanesulfonamide

Step 1. Preparation of 1-Chloro-4-(2-tetrahydropyranyloxy)nonane

To a stirred solution of 1-chloro-4-hydroxynonane (Example A, Step 2) (11.0 g., 0.062 mole) and dihydropyrane (5.2 g., 0.062 mole) cooled in an ice bath is added 5 drops of hydrochloric acid (conc.). A slight exothermic reaction is noted and when this is complete the reaction is allowed to come to room temperature, then stand for 2 hours. At the end of this period several pellets of sodium hydroxide are added and the reaction is distilled in vacuo. The yield of 1-chloro-4-(2-tetrahydropyranyloxy)nonane is 12.5 g. (77%), boiling 96°–102°/0.1 mm. Upon redistillation a boiling point of 90°–92°/0.1 mm. is obtained.

Step 2. Preparation of N-[4-(2-Tetrahydropyranyloxy)nonyl]phthalimide

Sodium hydride (53%) (1.5 g. excess) is washed with benzene three times by decantation, then dimethyl formamide (100 ml.) is added. To this stirred suspension is added a solution of phthalimide (4.3 g., 0.03 mole) in dimethyl formamide (50 ml.) at such a rate as to keep the temperature below 35° C. A clear solution is obtained and to it is added 1-chloro-4-(2-tetrahydropyranyloxy)nonane (7.8 g. 0.03 mole) and the resulting solution is stirred and heated at 95° C. for 20 hours. The reaction is then concentrated to one-half its volume in vacuo, poured into ice water (200 ml.) and extracted with ether (2 × 150 ml.). The ether is washed with 5% sodium hydroxide (2 × 50 ml.), saturated sodium chloride solution (2 × 50 ml.), then dried over sodium sulfate. Evaporation of the ether affords 4.5 g. (45% yield) of N-[4-(2-tetrahydropyranyloxy)nonyl]phthalimide melting 59°–61° C. After crystallization from cyclohexane the product melts at 62°–63° C. Anal. Calcd. for $C_{22}H_{31}NO_4$: C, 70.75; H, 8.36; N, 3.75 Found: C, 71.03; H, 8.28; N, 3.81

Step 3. Preparation of 4-(2-tetrahydropyranyloxy)nonylamine

To a solution of N-[4-(2-tetrahydropyranyloxy) nonyl]-phthalimide (33.0 g., 0.88 mole) in absolute ethanol (300 ml.), is added hydrazine (64%) (10 ml. excess) and the reaction is heated at reflux for 1.5 hours. An additional 5 ml. of hydrazine (64%) is added and reflux continued for 1.5 hours. The reaction is cooled to room temperature and the white solid that is present is removed by filtration. The filtrate is concentrated in vacuo to 75 ml., then poured into water (200 ml.). The solution is made basic with 5% sodium hydroxide and then extracted with ether (3 × 100 ml.). The ether layer is washed with saturated sodium chloride solution, then dried over sodium sulfate. The ether is removed in vacuo and the resulting oil is distilled. The yield of 4-(2-tetrahydropyranyloxy)nonylamine is 16.0 g. (75%), boiling 100°–102°/0.1 mm.

Anal. Calcd. for $C_{14}H_{29}NO_2$: C, 69.08; H, 12.01; N, 5.75 Found: C, 68.58; H, 12.42; N, 5.66

Step 4. Preparation of N-[4-(2-Tetrahydropyranyloxy)nonyl]methanesulfonamide To a stirred, ice cold solution of 4-(2-tetrahydropyranyloxy)nonylamine (7.29 g., 0.03 mole) in pyridine (40 ml.) is added methanesulfonylchloride (3.42 g., 0.03 mole) at such a rate as to maintain the reaction temperature at 5°–10° C. The reaction is then allowed to stand at room temperature for 6 hours, poured into ice water (200 ml.) and extracted with ether (2 × 100 ml.). The ether is washed with ice cold 5% hydrochloric acid (2 × 20 ml.), with brine (2 × 25 ml.), and then dried over sodium sulfate. Evaporation in vacuo affords N-[4-(2-tetrahydropyranyloxy)nonyl]methanesulfonamide as a pale yellow liquid.

O. Preparation of Ethyl 7-(methanesulfonamido)heptanoate

A stirred suspension of sodium hydride (57%) (2.33 g., 0.055 mole) in a solvent mixture of benzene (50 ml.) and dimethylformamide (50 ml.) is treated, over 30 minutes with methanesulfonamide (4.75 g., 0.055 mole). This mixture is heated on the steam bath for 1.5 hours, then cooled to room temperature. At this temperature is added ethyl 7-bromoheptanoate (13 g., 0.055 mole) and the reaction is heated at 90° C. for twenty hours. The reaction is poured into water (200 ml.), neutralized with hydrochloric acid and extracted with ethyl acetate (2 × 100 ml.). The ethyl acetate layer is washed with brine, dried over sodium sulfate, then concentrated in vacuo. The yield of ethyl 7-(methanesulfonamido)heptanoate is 7.1 g. (51%) boiling 165°–168°/0.1 mm.

Anal. Calcd. for $C_{10}H_{21}NO_4S$: C, 47.78; H, 8.42; N, 5.57 Found: C, 47.05; H, 8.51; N, 5.41

P. Preparation of Ethyl 7-(ethanesulfonamido)heptanoate

The synthesis of this compound is carried out as described in Example O except that the methanesulfonamide is replaced by an equimolar amount of ethanesulfonamide. Ethyl 7-(ethanesulfonamido)heptanoate is obtained as a pale yellow oil upon evaporation of the ethyl acetate extracts.

Q. Preparation of Ethyl 7-(Propanesulfonamido)heptanoate

By following the procedure described in Example O but substituting propanesulfonamide for methanesulfonamide there is obtained ethyl 7-(propanesulfonamido)-heptanoate.

R. Preparation of Ethyl 7-[(1-methylethane)sulfonamido]heptanoate

By following the procedure described in Example O but substituting 1-methylethanesulfonamide for methanesulfonamide there is obtained ethyl 7-[(1-methylethane)sulfonamido]heptanoate.

S. Preparation of 1-Chloro-4-acetoxy-4-methylnonane

The Grignard reagent prepared from iodomethane (14.2 g., 0.1 mole) and magnesium (2.4 g., 0.1 mole) in ether solution is added, dropwise to an ether solution of 1-chloro-4-nonanone (Example A, Step 1) (17.6 g., 0.1 mole). The reaction is refluxed gently for 3 hours then cooled and poured carefully into ice water (300 ml.). The ether layer is separated, washed with brine, and dried over sodium sulfate. Removal of the ether in vacuo gives 1-chloro-4-hydroxy-4-methylnonane as an oil. The tertiary alcohol is dissolved in pyridine and treated with one molar equivalent of acetic anhydride at 60°-80° for 8-16 hours to give 1-chloro-4-acetoxy-4-methylnonane as a colorless oil.

T. Preparation of Ethyl 7-(methanesulfinamido)heptanoate

The synthesis of this compound is carried out as described in Example O except that the methanesulfonamide is replaced by an equimolar amount of methanesulfinamide. The ethyl 7-(methanesulfinamido)heptanoate is obtained as a yellow liquid upon evaporation of the ethyl acetate extracts.

U. Preparation of 1-Acetoxy-1-(3-bromo-1-propynyl)cyclohexane

Step 1. Preparation of 1-Acetoxy-1-ethynylcyclohexane

1-Ethynylcyclohexan-1-ol (100 g., 0.8 mole) is added dropwise with stirring to a mixture of acetic anhydride (86.7 g., 0.85 mole) and sulfuric acid (0.25 ml.). The temperature of the reaction mixture is kept at 10°-12° C. during the addition by means of an ice bath. The mixture is then stirred without cooling for 1.5 hours. It is then poured into 300 ml. of ice water. The oily product is taken up in ether, washed with water, dilute sodium bicarbonate solution and brine and dried over sodium sulfate. Distillation affords 107 g. (80%) of 1-acetoxy-1-ethynylcyclohexane, b.p. 95°-97° C./15 mm.

Step 2. Preparation of 1-Acetoxy-1-(3-diethylamino-1-propynyl)cyclohexane

A mixture of 1-acetoxy-1-ethynylcyclohexane (64.00 g., 0.385 mole), diethylamine (30.95 g., 0.424 mole), paraformaldehyde, (15.00 g.; 0.500 mole), cuprous chloride (1.5 g.) and dioxane (60 ml.) is stirred well. An exothermic reaction gradually results which may require external cooling to prevent spillage. After this initial reaction, the mixture is heated on a steam bath for 1½ hours.

The cooled reaction mixture is treated with ether and the product is extracted into ice-cold 5% hydrochloric acid. This cold aqueous acidic solution is then basified with ice-cold 10% sodium hydroxide. The oily amine is extracted with ether and the combined extracts are washed with saturated sodium chloride solution and then dried over anhydrous sodium sulfate. The solvent is removed under vacuum and the residual oil is distilled to give 72.7 g. (75%) of light yellow oil, b.p. 113°-115° C./0.15 mm.; pmr (CDCl$_3$) 1.07 (6H,t), 2.02 (3H,s CH$_3$COO), 2.60 (4H,q CH$_3$CH$_2$N), 3.52 (2H,s CH$_2$C—).

Step 3. Preparation of 1-Acetoxy-1-(3-bromo-1-propynyl)cyclohexane

Cyanogen bromide (31.8 g., 0.3 mole) is added to a solution of 1-acetoxy-1-(3-diethylamino)-1-propynyl)-cyclohexane (61 g., 0.24 mole) in ether (250 ml.) and the resulting solution is allowed to stand at 25°-27° C. for 18 hours. The ether solution is washed with 5% hydrochloric acid solution, water and brine and dried over sodium sulfate. The ether is evaporated and the residual oil distilled. There is obtained 34.8 g. (55%) of 1-acetoxy-1-(3-bromo-1-propynyl)cyclohexane, a slightly yellowish oil, b.p. 114°-120° C./0.2 mm.

V. Preparation of 1-Acetoxy-1-(3-bromo-1-propynyl)cyclooctane

By the following the procedure described in Example U but substituting in Step 1 1-ethynylcyclooctan-1-ol for 1-ethynylcyclohexan-1-ol there are obtained successively 1-acetoxy-1-(3-diethylamino-1-propynyl)cyclooctane (Step 2), and 1-acetoxy-1-(3-bromo-1-propynyl)cyclooctane (Step 3).

W. Preparation of 1-Bromo-4-acetoxy-4-propyl-2-heptyne

Step 1. Preparation of 3-Acetoxy-3-propyl-1-hexyne

3-Propyl-1-hexyn-3-ol (98.0 g., 0.7 mole) is added dropwise with stirring to a mixture of acetic anhydride (79.5 g., 0.78 mole) and sulfuric acid (0.25 ml.) during 50 min. the temperature rises to 50° C. The mixture is allowed to stand 18 hours and is then poured into 300 ml. of ice water. The oily product is taken up in ether, washed with water, dilute sodium bicarbonate solution and brine and dried over sodium sulfate. Distillation yields 108.5 g. (86%) of 3-acetoxy-3-propyl-1-hexyne, b.p. 93°-95° C./17 mm.

Step 2. Preparation of 1-Diethylamino-4-acetoxy-4-propyl-2-heptyne

A mixture of 3-acetoxy-3-propyl-1-hexyne (115.2 g., 0.634 mole), diethylamine (51 g., 0.7 mole), paraformaldehyde (24.9 g., 0.83 mole) and dioxane (120 ml.) is stirred and heated on the steam bath for 2 hours. The reaction mixture is cooled, treated with ether and the product extracted into ice-cold 5% hydrochloric acid. The cold acidic solution is then basified with ice-cold 10% sodium hydroxide. The oily amine is taken up in ether, washed with water and brine and dried over sodium sulfate. Distillation yields 99.5 g. (59%) of the amine product, b.p. 101°-110° C./0.1 mm.

Step 3. Preparation of 1-Bromo-4-acetoxy-4-propyl-2-heptyne

Cyanogen bromide (46.6 g.; 0.44 mole) is added to a solution of 1-diethylamino-4-acetoxy-4-propyl-2-heptyne (99.0 g., 0.371 mole) in ether (400 ml.) and the resulting solution is allowed to stand at 25°-27° C. for 16 hours. The ether solution is washed with 5% hydrochloric acid solution, water and brine and dried over sodium sulfate. The ether is evaporated and the residual oil distilled. There is obtained 70.0 g. (69%) of 1-bromo-4-acetoxy-4-propyl-2-heptyne, a colorless oil, b.p. 106°-107° C./0.1 mm.

Anal. Calcd. for $C_{12}H_{19}BrO_2$: C, 52.88; H, 6.96; Found: C, 52.00; H, 6.91.

EXAMPLE 1

Preparation of 7-[N-(4-Hydroxynonyl)methanesulfonamido]heptanoic Acid

STEP A: Preparation of Ethyl 7-[N-(4-Acetoxynonyl)methanesulfonamido]heptanoate Sodium hydride (0.715 g., 0.0298 mole) is suspended in benzene (30 ml.) and dimethylformamide (30 ml.). Ethyl 7-(methanesulfonamido)heptanoate (6.8 g., 0.0271 mole) (Example O, Step 1) is added and the suspension heated on the steam bath for 15 minutes. After cooling to room temperature, 1-chloro-4-acetoxynonane (6.55 g., 0.0298 mole) (Example A, Step 3) is added over 15 minutes and the resulting solution heated on the steam bath for 20 hours. Then the reaction is poured into water (300 ml.) and extracted with ethyl acetate (3 × 100 ml.). The organic layer is washed with brine (2 × 50 ml.), dried over sodium sulfate then concentrated in vacuo to an oil which is purified by chromatography on silica gel. The silica gel is eluted with 3% methanol in chloroform and evaporation of the appropriate fraction affords ethyl 7-[N-(4-acetoxynonyl)methanesulfonamido]heptanoate. The yield is 6.0 g. (51%).

Analysis calculated for $C_{21}H_{41}NO_6S$: C, 57.90; H, 9.49; N, 3.22 Found: C, 58.08; H, 9.99; N, 2.99

STEP B: Preparation of 7-[N-(4-Hydroxynonyl)methanesulfonamido]heptanoic Acid A solution composed of ethyl 7-[N-(4-acetoxynonyl)methanesulfonamido]heptanoate (6.0 g., 0.0134 mole), sodium hydroxide (1.66 g., 0.0414 mole), water (9 ml.), and ethanol (81 ml.) is kept at room temperature for 20 hours. Most of the solvent is removed in vacuo, water (150 ml.) is added and the solution extracted with ethyl acetate (100 ml.). Then the aqueous layer is acidified (hydrochloric acid) and extracted again with ethyl acetate (2 × 75 ml.). The organic layer is dried over sodium sulfate then concentrated in vacuo to yield 7-[N-(4-hydroxynonyl)methanesulfonamido]heptanoic acid. The yield is 4.3 g. (88%).

Analysis calculated for $C_{17}H_{35}NO_5S$: C, 55.86; H, 9.65; N, 3.83 Found: C, 56.07; H, 9.77; N, 3.65

EXAMPLE 2

Preparation of 7-[N-(4-Hydroxy-2-nonynyl)methanesulfonamido]heptanoic Acid

The synthesis of this compound is carried out as described in Example 1 except that, in Step A, the 1-chloro-4-acetoxynonane is replaced by an equimolar amount of 1-bromo-4-acetoxy-2-nonyne (Example I, Step 3). The product of Step A is thus ethyl 7-[N-(4-acetoxy-2-nonynyl)methanesulfonamido]heptanoate.

Analysis calculated for $C_{21}H_{37}NO_6S$: C, 58.44; H, 8.64; N, 3.25 Found: C, 57.92; H, 9.15; N, 3.20

The subsequent step yields 7-[N-(4-hydroxy-2-nonynyl)methanesulfonamido]heptanoic acid (B).

Analysis calculated for $C_{17}H_{31}NO_5S$: C, 56.48; H, 8.64; N, 3.88 Found: C, 56.42; H, 9.03; N, 3.68

EXAMPLE 3

Preparation of 7-[N-(4(R)-Hydroxynonyl)methanesulfonamido]heptanoic Acid

The synthesis of this compound is carried out as described in Example 1 except that, in Step A, the 1-chloro-4-acetoxynonane is replaced by an equimolar amount of 1-bromo-4(R)-acetoxy-2-nonyne (Example J). The product of Step A is thus ethyl 7-[N-(4(R)-acetoxy-2-nonynyl)methanesulfonamido]heptanoate, $[\alpha]_D^{36} + 46°$ [C 2.95, $CHCl_3$].

Analysis calculated for $C_{21}H_{37}NO_6S$: C, 58.44; H, 8.64; N, 3.25 Found: C, 58.77; H, 8.98; N, 3.13

The subsequent step yields 7-[N-(4(R)-hydroxy-2-nonynyl)methanesulfonamido]heptanoic acid (B), $[\alpha]_D^{26} + 0.93°$ [C 3.3, $CHCl_3$].

Analysis Calculated for $C_{17}H_{31}NO_5S$: C, 56.48; H, 8.64; N, 3.88 Found: C, 55.96; H, 9.13; N, 3.85

The product of Step B is hydrogenated over a platinum on charcoal catalyst to afford 7-[N-(4(R)-hydroxynonyl)methanesulfonamido]heptanoic acid, $[\alpha]_D^{26} - 3.0°$ [C 3.72, $CHCl_3$].

Analysis calculated for $C_{17}H_{35}NO_5S$: C, 55.86; H, 9.65; N. 3.83 Found: C, 55.62; H, 9.76; N, 3.70

EXAMPLE 4

Preparation of 7-[N-(4(S)-Hydroxynonyl)methanesulfonamido]heptanoic Acid

The synthesis of this compound is carried out as described in Example 1 except that, in Step A, the 1-chloro-4-acetoxynonane is replaced by an equimolar amount of 1-bromo-4(S)-acetoxy-2-nonyne (Example K). The product of Step A is thus ethyl 7-[N-(4(S)-acetoxy-2-nonynyl)methanesulfonamido]heptanoate, $[\alpha]_D^{26} - 48.8°$ [C 2.865, $CHCl_3$].

Analysis calculated for $C_{21}H_{37}NO_6S$: C, 58.44; H, 8.64; N, 3.25 Found: C, 58.72; H, 9.15; N, 3.13

The subsequent step yields 7-[N-(4(S)-hydroxy-2-nonynyl)methanesulfonamido]heptanoic acid (B), $[\alpha]_D^{26} - 0.53°$ [C 3.015, $CHCl_3$].

Analysis calculated for $C_{17}H_{31}NO_5S$: C, 56.48; H, 8.64; N, 3.88 Found: C, 56.30; H, 8.61; N, 3.79

The product of Step B is hydrogenated over a platinum on charcoal catalyst to afford 7-[N-(4(S)-hydroxynonyl)methanesulfonamido]heptanoic acid, $[\alpha]_D^{26} + 3.92°$ [C 2.44, $CHCl_3$].

Analysis calculated for $C_{17}H_{35}NO_5S$: C, 55.86; H, 9.65; N, 3.83 Found: C, 55.45; H, 9.40; N, 3.74

EXAMPLE 5

Preparation of 7-[N-(4-Hydroxynonyl)ethanesulfonamido]heptanoic Acid

The synthesis of this compound is carried out as described in Example 1 except that, in Step A, the ethyl 7-(methanesulfonamido)heptanoate is replaced by an equimolar amount of ethyl 7-ethanesulfonamidoheptanoate (Example P). The product of Step A is thus ethyl 7-[N-(4-acetoxynonyl)ethanesulfonamido]heptanoate. The subsequent step yields 7-[N-(4-hydroxynonyl)ethanesulfonamido]heptanoic acid (B).

EXAMPLE 6

Preparation of
7-[N-(4-Hydroxynonyl)propanesulfonamido]heptanoic Acid

The synthesis of this compound is carried out as described in Example 1 except that, in Step A, the ethyl 7-(methanesulfonamido)heptanoate is replaced by an equimolar amount of ethyl 7-(propanesulfonamido)heptanoate (Example Q). The product of Step A is thus ethyl 7-[N-(4-acetoxynonyl)propanesulfonamido]heptanoate. The subsequent hydrolysis step yields 7-[N-(4-hydroxynonyl)propanesulfonamido]heptanoic acid (B).

EXAMPLE 7

Preparation of
7-[N-(4-Hydroxynonyl)-1-methylethanesulfonamido]-heptanoic Acid

The synthesis of this compound is carried out as described in Example 1 except that, in Step A, the ethyl 7-(methanesulfonamido)heptanoate is replaced by an equimolar amount of ethyl 7-[(1-methylethane)sulfonamido]heptanoate (Example R). The product of Step A is thus ethyl 7-[N-(4-acetoxynonyl)-1-methylethanesulfonamido]heptanoate. The subsequent step yields 7-[N-(4-hydroxynonyl)-1-methylethanesulfonamido]heptanoic acid (B).

EXAMPLE 8

Preparation of
7-[N-(4-Hydroxynonyl)methanesulfonamido]-2-methylheptanoic Acid

STEP A: Preparation of Ethyl
7-{N-[4-(2-Tetrahydropyranyloxy)nonyl]methanesulfonamido}-2-methylheptanoate A stirred suspension of sodium hydride (57%) (5.0 g., excess) in a solvent mixture of benzene (75 ml.) and dimethylformamide (75 ml.) is treated, over 30 minutes, with N-[4-(2-tetrahydropyranyloxy)nonyl]methanesulfonamide (Example N, Step 4) (32.1 g., 0.1 mole) dissolved in benzene (20 ml.). Stirring is continued for 1 hour. Then ethyl 7-bromo-2-methylheptanoate (Example L, Step 4) (25.3 g., 0.1 mole) is added dropwise, and the reaction is heated on the steam bath for 6 hours. The cooled reaction mixture is poured into water (400 ml.) and extracted with ethyl acetate (2 × 200 ml.). The organic fractions are combined, washed with brine, then dried over sodium sulfate. The solvents are removed in vacuo to give 7-{N-[4-(2-tetrahydropyranyloxy)nonyl]methanesulfonamido}-2-methylheptanoate as a pale yellow liquid.

STEP B: Preparation of
7-[N-(4-Hydroxynonyl)methanesulfonamido]-2-methylheptanoic Acid A solution is prepared from ethyl 7-{N-[4-(2-tetrahydropyranyloxy)nonyl]methanesulfonamido}-2-methylheptanoate (4.9 g., 0.01 mole), ethanol (50 ml.), and 4 drops of hydrochloric acid (conc.), and kept at ambient temperature for 4.5 hours. Then to the reaction is added a solution of sodium hydroxide (0.72 g., 0.018 mole) in water (10 ml.) and the reaction is kept at ambient temperature for an additional 20 hours. Most of the ethanol is removed in vacuo and the residue dissolved in water (100 ml.). The solution is extracted once with ether (75 ml.) then acidified with hydrochloric acid (dil.). The oil that separates is extracted into ether, the ether is washed with brine, dried over sodium sulfate, then removed under vacuum to give 7-[N-(4-hydroxynonyl)methanesulfonamido]-2-methylheptanoic acid as a yellow liquid.

EXAMPLE 9

Preparation of
7-[N-(4-Hydroxynonyl)methanesulfonamido]-2,2-dimethylheptanoic Acid The synthesis of this compound is carried out as described in Example 8 except that, in Step A, the ethyl 7-bromo-2-methylheptanoate is replaced by an equimolar amount of methyl 2,2-dimethyl-7-iodoheptanoate. The product of Step A is thus methyl 7-{N-[4-(2-tetrahydropyranyloxy)nonyl]methanesulfonamido}-2,2-dimethylheptanoate. The subsequent step yields 7-[N-(4-hydroxynonyl)methanesulfonamido]-2,2-dimethylheptanoic acid (B).

EXAMPLE 10

Preparation of
7-[N-(4-Hydroxynonyl)methanesulfonamido]-3-methylheptanoic Acid

The synthesis of this compound is carried out as described in Example 8 except that, in Step A, the ethyl 7-bromo-2-methylheptanoate is replaced by an equimolar amount of methyl 3-methyl-7-iodoheptanoate. The product of Step A is thus methyl 7-{N-[4-(2-tetrahydropyranyloxy)nonyl]methanesulfonamido}-3-methylheptanoate. The subsequent hydrolysis step yields 7-[N-(4-hydroxynonyl)methanesulfonamido]-3-methylheptanoic acid (B).

EXAMPLE 11

Preparation of 7-[N-(4-Hydroxynonyl)methanesulfonamido]-3,3-dimethylheptanoic Acid The synthesis of this compound is carried out as described in Example 8 except that, in Step A, the ethyl 7-bromo-2-methylheptanoate is replaced by an equimolar amount of methyl 3,3-dimethyl-7-iodoheptanoate. The product of Step A is thus methyl 7-N-[4-(2-tetrahydropyranyloxy)nonyl]methanesulfonamido-3,3-dimethylheptanoate. The subsequent step yields 7-[N-(4-hydroxynonyl)methanesulfonamido]-3,3-dimethylheptanoaic acid (B).

EXAMPLE 12

Preparation of
4-[N-(4-Hydroxynonyl)methanesulfonamido]-butoxyacetic Acid

The synthesis of this compound is carried out as described in Example 8 except that, in Step A, the ethyl 7-bromo-2-methylheptanoate is replaced by an equimolar amount of ethyl 4-bromobutoxyacetate (Example M). The product of Step A is thus ethyl 4-{N-[4-(2-tetrahydropyranyloxy)nonyl]methanesulfonamido}butoxyacetate. The subsequent step yields 4-[N-(4-hydroxynonyl)methanesulfonamido]butoxyacetic acid (B).
Anal. Calcd. for $C_{16}H_{33}NO_6S$: C, 52.29; H, 9.05; N, 3.81;
Found: C, 52.04; H, 8.90; N, 3.81

EXAMPLE 13

Preparation of 7-[N-(4-Hydroxy-8-methylnonyl)methanesulfonamido]heptanoic Acid

The synthesis of this compound is carried out as described in Example 1 except that, in Step A, the 1-chloro-4-acetoxy-8-methylnonane (Example B, Step 3). The product of Step A is thus ethyl 7-[N-(4-acetoxy-8-methylnonyl)methanesulfonamido]heptanoate. The subsequent step yields 7-[N-(4-hydroxy-8-methylnonyl)methanesulfonamido]heptanoic acid (B).

EXAMPLE 14

Preparation of 7-[N-(4-Hydroxyundecyl)methanesulfonamido]heptanoic Acid

The synthesis of this compound is carried out as described in Example 1 except that, in Step A, the 1-chloro-4-acetoxynonane is replaced by an equimolar amount of 1-chloro-4-acetoxyundecane (Example C, Step 3). The product of Step A is thus ethyl 7-[N-(4-acetoxyundecanyl)methanesulfonamido]heptanoate. The subsequent step yields 7-[N-(4-hydroxyundecanyl)methanesulfonamido]heptanoic acid (B).

EXAMPLE 15

Preparation of 7-[N-(4-Hydroxy-8,8-dimethylnonyl)methanesulfonamido]heptanoic Acid The synthesis of this compound is carried out as described in Example 1 except that, in Step A, the 1-chloro-4-acetoxynonane is replaced by an equimolar amount of 1-chloro-4-acetoxy-8,8-dimethylnonane (Example D). The product of Step A is thus ethyl 7-[N-(4-acetoxy-8,8-dimethylnonyl)methanesulfonamido]heptanoate. The subsequent step yields 7-[N-(4-hydroxy-8,8-dimethylnonyl)methanesulfonamido]heptanoic acid (B).

EXAMPLE 16

Preparation of 7-[N-(4-Hydroxy-9,9,9-trifluorononyl)methanesulfonamido]heptanoic Acid The synthesis of this compound is carried out as described in Example 1, except that, in Step A, the 1-chloro-4-acetoxy-9,9,9-trifluorononane (Example E). The product of Step A is thus ethyl 7-[N-(4-acetoxy-9,9,9-trifluorononyl)methanesulfonamido]heptanoate. The subsequent step yields 7-[N-(4-hydroxy-9,9,9-trifluorononyl)methanesulfonamido]heptanoic acid (B).

EXAMPLE 17

Preparation of 7-[N-(4-Hydroxy-8-nonenyl)methanesulfonamido]heptanoic Acid.

The synthesis of this compound is carried out as described in Example 1 except that, in Step A, the 1-chloro-4-acetoxynonane is replaced by an equimolar amount of 1-chloro-4-acetoxy-8-nonene. The product of Step A is thus ethyl 7-[N-(4-acetoxy-8-nonenyl)methanesulfonamido]heptanoate. The subsequent step yields 7-[N-(4-hydroxy-8-nonenyl)methanesulfonamido]heptanoic acid (B).

EXAMPLE 18

Preparation of 7-[N-(4-Hydroxy-5,5-dimethylnonyl)methanesulfonamido]heptanoic Acid The synthesis of this compound is carried out as described in Example 1 except that, in Step A, the 1-chloro-4-acetoxynonane is replaced by an equimolar amount of 1-chloro-4-acetoxy-5,5-dimethylnonane (Example G). The product of Step A is thus ethyl 7-[N-(4-acetoxy-5,5-dimethylnonyl)methanesulfonamido]heptanoate. The subsequent step yields 7-[N-(4-hydroxy-5,5-dimethylnonyl)methanesulfonamido]heptanoic acid (B).

EXAMPLE 19

Preparation of 7-[N-(4-Hydroxy-(E)-2-nonenyl)methanesulfonamido]heptanoic Acid

The synthesis of this compound is carried out as described in Example 1 except that, in Step A, the 1-chloro-4-acetoxynonane is replaced by an equimolar amount of 1-bromo-4-acetoxy-2-nonene (Example H). The product of Step A is thus ethyl 7-[N-(4-acetoxy-(E)-2-nonenyl)methanesulfonamido]heptanoic acid (B).

EXAMPLE 20

Preparation of 7-[N-(4-Hydroxy-4-methylnonyl)methanesulfonamido]heptanoic Acid

The synthesis of this compound is carried out as described in Example 1 except that, in Step A, the 1-chloro-4-acetoxynonane is replaced by an equimolar amount of 1-chloro-4-acetoxy-4-methylnonane (Example S). The product of Step A is thus ethyl 7-[N-(4-acetoxy-4-methylnonyl)methanesulfonamido]heptanoate. The subsequent step yields 7-[N-(4-hydroxy-4-methylnonyl)methanesulfonamido]heptanoic acid (B).

EXAMPLE 21

Preparation of 7-[N-(4-Hydroxynonyl)methanesulfinamido]heptanoic Acid

The synthesis of this compound is carried out as described in Example 1 except that, in Step A, the ethyl 7-(methanesulfonamido heptanoate is replaced by an equimolar amount of ethyl 7-(methanesulfinamido)heptanoate (Example T). The product of Step A is thus ethyl 7-[N-(4-acetoxynonyl)methanesulfinamido]heptanoate. The subsequent step yields 7-[N-(4-hydroxynonyl)methanesulfinamido]heptanoic acid (B).

EXAMPLE 22

Preparation of Methyl 7-[N-(4-Hydroxynonyl)methanesulfonamido]heptanoic Acid

A solution of diazomethane (approx. 2.5 g., 0.06 mole) in ether (100 ml.) is mixed with a solution of 7-[N-(4-hydroxynonyl)methanesulfonamido]heptanoic acid (10.8 g., 0.03 mole) (Example 1, Step B) in ether (50 ml.). The resulting solution is allowed to stand at room temperature for 4 hours. Acetic acid is then added to destroy the excess diazomethane and the solution is washed with dilute sodium bicarbonate solution and water and dried over sodium sulfate. Evaporation of volatile materials at reduced pressure yields methyl 7-[N-(4-hydroxynonyl)methanesulfonamido]heptanoate as a viscous oil.

EXAMPLE 23

Preparation of Decyl 7-[N-(4-Hydroxynonyl)methanesulfonamido]heptanoate

Using the method of Example 22 but substituting an ether solution of 1-diazodecane for the ether solution of diazomethane, there is obtained decyl 7-[N-(4-hydroxynonyl)methanesulfonamido]heptanoate, as a viscous oil.

EXAMPLE 24

Preparation of N-[(2-Dimethylamino)ethyl]-7-[N-(4-hydroxynonyl)-methanesulfonamido]heptanamide A solution of 7-[N-(4-hydroxynonyl)methanesulfonamido]heptanoic acid (3.65 g., 10 millimoles) (Example 1, Step B), triethylamine (1.74 ml., 12.5 millimoles) and distilled water (18 ml.) in acetonitrile (100 ml.) is treated with N-t-butyl-5-methyl-isoxazolium perchlorate (3.0 g., 12.5 millimoles). The resulting solution is evaporated in vacuo at 20°–25° C. over 4 hours providing a tacky residue which is triturated with water (150 ml.) at 0°–5° C. for 15 minutes. After decanting the aqueous phase, the oily residue is dissolved in benzene-ether [(1:1), 200 ml.]. The organic extract is dried over sodium sulfate, then evaporated in vacuo providing the desired "active ester".

A solution of 2-dimethylaminoethylamine (0.88 g., 10 millimoles) in acetonitrile (25 ml.) is added to a solution of the "active ester" in acetonitrile (25 ml.) and the solution is stirred at 25° C. for 17 hours. The solvent is removed in vacuo, the residual oil is partitioned between ether (200 ml.) and water (200 ml.). The ether layer is extracted with 5% hydrochloric acid (2 × 50 ml.). The aqueous acid phase is made basic with aqueous sodium carbonate then extracted with ether. The ether extract is washed with brine solution (100 ml.), dried over sodium sulfate, evaporated in vacuo leaving the N-[(2-dimethylamino)ethyl]-7-[N-(4-hydroxynonyl)methanesulfonamido]heptanamide as a viscous oil.

EXAMPLE 25

Preparation of 7-[N-(4-Hydroxynonyl)methanesulfonamido]heptanamide

Using the method of Example 24 but substituting an acetonitrile solution of ammonia for the acetonitrile solution of 2-dimethylaminoethylamine, there is obtained 7-[N-(4-hydroxynonyl)methanesulfonamido]heptanamide.

EXAMPLE 26

Preparation of 7-[N-(4-Acetoxynonyl)methanesulfonamido]heptanoic Acid

A mixture of 7-[N-(4-hydroxynonyl)methanesulfonamido]heptanoic acid (10.9 g., 0.03 mole) (Example 1, Step B) and acetic anhydride (6.1 g., 0.06 mole) is heated at 60° C. for 18 hours. The mixture is cooled and taken up in 80 ml. of ethyl ether. The solution is extracted with an ice-cold solution of 8 g. of sodium hydroxide in 150 ml. of water. The basic solution is separated and acidified with concentrated hydrochloric acid. The crude product that separates is extracted into ether, washed with water and dried over sodium sulfate. The ether is evaporated and the residual oil is purified by chromatography on silica gel using 2% methanol in chloroform as the eluting solvent. There is obtained 7-[N-(4-acetoxynonyl)methanesulfonamido]heptanoic acid as a viscous oil.

By substituting for the acetic anhydride used in Example 26, an equivalent amount of acetic formic anhydride, propionic anhydride, butyric anhydride, isobutyric anhydride, valeric anhydride, or pivalic anhydride and conducting the reaction as described in Example 21, there is obtained 7-[N-(4-formyloxynonyl)sulfonamido]heptanoic acid, 7-[N-(4-propionyloxynonyl)-sulfonamido]heptanoic acid, 7-[N-(4-butyryloxynonyl)-sulfonamido]heptanoic acid, 7-[N-(4-isobutyryloxynonyl)sulfonamido]heptanoic acid, 7-[N-(4-valeryloxynonyl)sulfonamido]heptanoic acid, and 7-[N-(4-pivaloyloxynonyl) sulfonamido]heptanoic acid, respectively.

EXAMPLE 27

Preparation of 7-{N-[3-(1-Hydroxycyclohexyl)propyl]methanesulfonamido}heptanoic Acid The synthesis of this compound is carried out as described in Example 3 except that, in Step A, the 1-bromo-4(R)-acetoxy-2-nonyne is replaced by an equimolar amount of 1-acetoxy-1-(3-bromo-1-propynyl)cyclohexane (Example U). The product of Step A is thus ethyl 7-{N-[3-(1-acetoxycyclohexyl)-2-propynyl]methanesulfonamido}heptanoate.

Anal. Calcd. for $C_{21}H_{35}NO_6S$: C, 58.72; H, 8.21; N, 3.26; Found: C, 59.05; H, 8.39; N, 3.05.

The subsequent step yields 7-{N-[3-(1-hydroxycyclohexyl)-2-propynyl]methanesulfonamido}heptanoic acid (B).

Anal. Calcd. for $C_{17}H_{29}NO_5S$: C, 56.80; H, 8.13; N, 3.90; Found: C, 56.24; H, 8.52; N, 3.51.

The hydrogenation step(c) yields 7-{N-[3-(1-hydroxycyclohexyl)propyl]methanesulfonamido}heptanoic acid (C).

Anal. Calc. for $X_{17}H_{33}NO_5S$: C, 56.17; H, 9.15; N, 3.85; Found: C, 56.01; H, 9.48; N, 3.73.

EXAMPLE 28

Preparation of 7-{N-[3-(1-Hydroxycyclooctyl)propyl]methanesulfonamido}heptanoic Acid The synthesis of this compound is carried out as described in Example 3, except that, in Step A, the 1-bromo-4(4)-acetoxy-2-nonyne is replaced by an equimolar amount of 1-acetoxy-1-(3-bromo-1-propynyl)cyclooctane (Example V). The product of Step A is thus ethyl 7-{[3-(1-acetoxycyclooctyl)-2-propynyl]methanesulfonamido}heptanoate. The subsequent steps yield 7-{N-[3-(1-hydroxycyclooctyl)-2-propynyl]methanesulfonamido}heptanoic acid (B) and 7-{N[3(1-hydroxycyclooctyl)propyl]methanesulfonamido}heptanoic acid (C).

EXAMPLE 29

Preparation of 7-[N-(4-Hydroxy-4-propylheptyl)methanesulfonamido]heptanoic Acid The synthesis of this compound is carried out as described in Example 3, except that, in Step A, the 1-bromo-4(R)-acetoxy-2-nonyne is replaced by an equimolar amount of 1-bromo-4-acetoxy-4-propyl-2-heptyne (Example W). The product of Step A is thus ethyl 7-[N-(4-acetoxy-4-propyl-2-heptynyl)methanesulfonamido]heptanoate. The subsequent steps yield 7-[N-(4-hydroxy-4-propyl-2-heptynyl)methanesulfonamido]heptanoic acid (B) and 7-[N-(4-hydroxy-4-propylhexyl)methanesulfonamido]heptanoic acid (C).

EXAMPLE 30

Capsule Formulation

| | |
|---|---|
| 7-[N-(4-hydroxynonyl)methanesulfonamido]heptanoic acid | 50 gm. |
| Stearic Acid (U.S.P. triple pressure | 125 gm. |
| Pluronic F-68 | 7.5 gm. |
| Corn Starch | 125 gm. |

The stearic acid and pluronic are united in a vessel and melted using water bath at 60°-65° C. The sulfonamido]heptanoic acid is dispersed into the mixture and the corn starch is added with stirring which is continued until the mixture cools to ambient temperature. The mixture is reduced to granules by screening and placed in a number 0 hard gelatin containing 307.5 mg. of total solids and 50 mg. of 7-[N-(4-hydroxynonyl)methanesulfonamido]heptanoic acid per capsule.

EXAMPLE 31

Parenteral Formulation of a Multidose Solution of Intramuscular and intravenous Use

| | |
|---|---|
| 7-{N-[3-(1-hydroxycyclohexyl)propyl]methanesulfonamido}-heptanoic acid | 1 gm. |
| Tris(hydroxymethyl)aminomethane (Reagent Grade Tham) | q.s. to adjust solution to pH 7.4 |
| Sodium chloride (U.S.P.) | q.s. to yield isotonic solution |
| Methylparaben | 10 mg. |
| Propylparaben | 1 mg. |
| Distilled water (pyrogen-free) | q.s. to 10 ml. |

The 7{N-[3-(1-hydroxycyclohexyl)propyl]methanesulfonamido]heptanoic acid suspended in about 6 ml. of the water is treated with tris(hydroxymethyl)aminoethane with stirring until the pH reaches 7.4. The methylparaben and propylparaben are added with stirring and sufficient sodium chloride added to produce an isotonic solution. After water is added to bring the final volume to 10 ml., the solution is sterilized by membrane filtration and placed in a vial by an aseptic technique. The solution contains the Tham salt of 7-{N-[3-(1-hydroxycyclohexyl)propyl]methanesulfonamido}heptanoic acid equivalent to 100 mg./ml. of the free acid.

EXAMPLE 32

Preparation of Suppositories

| | |
|---|---|
| 7-[N-(4(S)-hydroxynonyl)methanesulfonamido]heptanoic acid | 100 gm. |
| Butylated hydroxyanisole | 82 mg. |
| Butylated hydroxytoluene | 82 mg. |
| Ethylenediamine tetraacetic acid | 163 mg. |
| Glycerine, U.S.P. | 128 gm. |
| Sodium chloride, microfine | 52.5 gm. |
| Polyethylene glycol 6000 | 128 gm. |
| Polyethylene glycol 4000 | 1269 gm. |

The polyethylene glycol 4000 and polyethylene glycol 6000 were placed in a vessel surrounded by a water bath at such a temperature required to maintain the melted contents at 60°-65° C. To themelt is added the butylated hydroxyanisole and butylated hydroxytoluene with stirring. Then the ethylenediamine tetraacetic acid and microfine sodium chloride are added to and dispersed in the mixture. The 7-[N-4(S)-hydroxynonyl)methanesulfonyl]heptanoic acid is then added and dispersed into the mixture. Finally, the temperature is lowered to 55°-60° C. and the glycerine added and dispersed.

While maintaining the temperature of 55°-60° C. and continuous mixing, the melt is dispersed into plastic suppository cavities of a conventional suppository cold-molding device. The suppositories thus prepared contain a total of 1.7778 gm. of contents of which 200 mg. are 7-[N-(4-hydroxy-8,8-dimethylnonyl)methanesulfonamido]heptanoic acid.

What is claimed is:

1. The compound of the formula:

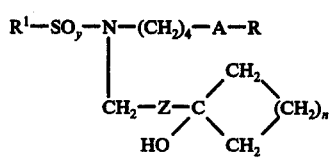

wherein
R is carboxy, a carboxy salt having the formula:

wherein Me⊕ is a pharmaceutically acceptable cation derived from a metal or an amine, or a carboxy ester having the formula:

wherein Y is alkyl having 1–10 carbon atoms, 1-succinimidoethyl, 1-(pivaloyloxy)ethyl, 2-acetamidoethyl, or diloweralkylamino-loweralkyl;

A is ethylene, trimethylene, α-methylethylene, β-methylethylene, α,α-dimethylethylene, or β,β-dimethylethylene;

$y$ is 1 or 2;

$R^1$ is methyl, ethyl, propyl, or isopropyl;

Z is ethylene, vinylene, or ethynylene; and $n$ is an integer of from 2 to 6 inclusive.

2. The compound of claim 1 wherein R is carboxy or a pharmaceutically acceptable carboxy salt.

3. The compound of claim 2 which has the formula:

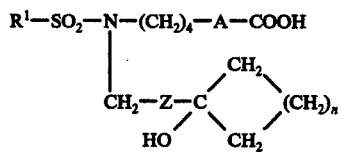

wherein $R^1$ is methyl, ethyl, propyl or isopropyl;

A is ethylene, trimethylene, α-methylethylene, β-methylethylene, α,α-dimethylethylene, β,β-dimethylethylene or oxymethylene; Z is ethylene or ethynylene, and $n$ is an integer of 2 to 6.

4. 7-{N-[3-(1-Hydroxycyclohexyl)propyl]methanesulfonamido}heptanoic acid, the compound of claim 3 wherein A and Z are ethylene, $R^1$ is acetyl and $n$ is 3.

5. 7-{N-[3-(1-Hydroxycyclohexyl)-2-propynyl]methanesulfonamido}heptanoic acid, the compound of claim 3 wherein A is ethylene, Z is ethynylene, $R^1$ is acetyl and $n$ is 3.

6. 7-{N-[3-(1-Hydroxycyclooctyl)propyl]methanesulfonamido}heptanoic acid, the compound of claim 3 wherein A and Z are ethylene, $R^1$ is acetyl and $n$ is 5.

7. A composition for improving renal function in animals with poorly functioning kidneys comprising an effective amount of the compound of claim 1 in a non-toxic pharmaceutically acceptable carrier.

8. The composition of claim 7 which is suitable for oral administration in tablet form.

9. The composition of claim 7 which is suitable for oral administration in capsule form.

10. The composition of claim 7 which is suitable for parenteral administration.

11. The composition of claim 7 which is suitable for use in suppository form.